United States Patent
Sobirey et al.

(10) Patent No.: US 9,457,010 B2
(45) Date of Patent: Oct. 4, 2016

(54) COMPOSITIONS FOR USE IN TREATING OR PREVENTING METABOLIC STRESS-INDUCED LUNG INJURY AND METHODS FOR INCREASING PHYSICAL CAPACITY OF MAMMALIAN LIVESTOCK

(71) Applicant: Nutri-fit GmbH & Co. KG, Muehlen (DE)

(72) Inventors: Michael Sobirey, Steinfeld (DE); Heinz Schneider, Cordast (CH)

(73) Assignee: Nutri-fit GmbH & Co. KG, Muehlen (DE)

( * ) Notice: Subject to any disclaimer, the term of this patent is extended or adjusted under 35 U.S.C. 154(b) by 0 days.

(21) Appl. No.: 14/643,487

(22) Filed: Mar. 10, 2015

(65) Prior Publication Data

US 2015/0182500 A1    Jul. 2, 2015

Related U.S. Application Data

(63) Continuation of application No. 12/892,431, filed on Sep. 28, 2010, now abandoned.

(30) Foreign Application Priority Data

Oct. 5, 2009  (EP) .................................... 09172235

(51) Int. Cl.
| | | |
|---|---|---|
| A61K 31/375 | (2006.01) | |
| A61K 31/355 | (2006.01) | |
| A61K 31/685 | (2006.01) | |
| A61K 31/14 | (2006.01) | |
| A61K 31/20 | (2006.01) | |

(52) U.S. Cl.
CPC ........... *A61K 31/375* (2013.01); *A23K 20/158* (2016.05); *A23K 20/174* (2016.05); *A23K 50/20* (2016.05); *A23K 50/30* (2016.05); *A61K 31/14* (2013.01); *A61K 31/20* (2013.01); *A61K 31/355* (2013.01); *A61K 31/685* (2013.01)

(58) Field of Classification Search
None
See application file for complete search history.

(56) References Cited

U.S. PATENT DOCUMENTS

| | | |
|---|---|---|
| 4,973,582 A | 11/1990 | Yoshida et al. |
| 5,198,216 A | 3/1993 | McGee |
| 5,215,750 A | 6/1993 | Keane, II |
| 5,571,527 A | 11/1996 | Nishimura et al. |
| 2004/0005311 A1 | 1/2004 | Pitman |

FOREIGN PATENT DOCUMENTS

| | | |
|---|---|---|
| DE | 19926554 A1 | 12/2000 |
| EP | 0877602 A1 | 11/1998 |
| WO | WO-99/65335 A1 | 12/1999 |
| WO | WO-02/24002 A2 | 3/2002 |
| WO | WO-02/34270 A1 | 5/2002 |
| WO | WO-03/061401 A2 | 7/2003 |
| WO | WO-03/090682 A2 | 11/2003 |
| WO | WO-2005073246 A2 | 8/2005 |

OTHER PUBLICATIONS

U.S. Appl. No. 12/892,431, filed Sep. 28, 2010.
Donnelly, "Corticosteroids and 'chronic' ARDS" Ir J Med Sci. 164(1):40-1 (1995).
Cranshaw, et al. "The pulmonary physician in critical care—part 9: non-ventilatory strategies in ARDS" Thorax. 57(9):823-9 (2002).
Grove et al., "Lipopolysaccharide (LPS) alters phosphatidylcholine metabolism in elicited peritoneal macrophages," J Leukoc Biol. 48(1):38-42 (1990).
"MAC-Jet Equine Racing International, Thoroughbred Super Fuel," <http://www.mac-jet.com/TBSF.html> Retrieved on Jan. 21, 2011 (2 pages).
"MAC-Jet Equine Racing International, MAC-Jet Quarter Horse Super Fuel," <(http://www.mac-jet.com/QHSF.html>, Retrieved on Jan. 21, 2011 (2 pages).
Martini et al., "Dietary effects on surfactant composition and pulmonary function," FASEB J. 13:A542 (1999).
Martini et al., "Lung surfactant kinetics in conscious pigs," Am J Physiol. 277(1 Pt 1):E187-95 (1999).
Martini et al., "Surfactant phosphatidylcholine in thermally injured pigs," Crit Care Med. 29(7):1417-22 (2001).
O'Callaghan et al., "Exercise-induced pulmonary haemorrhage in the horse: results of a detailed clinical, post mortem and imaging study. II. Gross lung pathology," Equine Vet J. 19(5):389-93 (1987).
O'Callaghan et al., "Exercise-induced pulmonary haemorrhage in the horse: results of a detailed clinical, post mortem and imaging study. II. Microscopic observations," Equine Vet J. 19(5):411-8 (1987).
Rivera et al., "A choline-rich diet improves survival in a rat model of endotoxin shock," Am J Physiol. 275(4 Pt 1):G862-7 (1998).
West et al., "Stress failure of pulmonary capillaries in racehorses with exercise-induced pulmonary hemorrhage," J Appl Physiol. 75(3):1097-109 (1993).
Wolfe et al., "Dietary fat composition alters pulmonary function in pigs," Nutrition. 18(7-8):647-53 (2002).
Wright et al., "Metabolism and turnover of lung surfactant," Am Rev Respir Dis. 136(2):426-44 (1987).

*Primary Examiner* — Anna Pagonakis
(74) *Attorney, Agent, or Firm* — Clark & Elbing LLP

(57) ABSTRACT

The present invention relates to a composition comprising (i) choline and (ii) a compound selected from the group consisting of palmitate, vitamin C and vitamin E for use in treating or preventing metabolic stress-induced lung injury and a method for increasing physical capacity of mammalian livestock comprising administering to the mammalian livestock the above composition.

5 Claims, No Drawings

COMPOSITIONS FOR USE IN TREATING OR PREVENTING METABOLIC STRESS-INDUCED LUNG INJURY AND METHODS FOR INCREASING PHYSICAL CAPACITY OF MAMMALIAN LIVESTOCK

CROSS REFERENCE TO RELATED APPLICATIONS

This application is a continuation of U.S. application Ser. No. 12/892,431, filed Sep. 28, 2010, which claims priority from prior foreign patent Application No. 09172235.5, filed Oct. 5, 2009 in Europe, both of which are hereby incorporated by reference.

The present invention relates to a composition comprising (i) choline and (ii) a compound selected from the group consisting of palmitate, vitamin C and vitamin E for use in treating or preventing metabolic stress-induced lung injury and a method for increasing physical capacity of mammalian livestock comprising administering to the mammalian livestock the above composition.

Metabolic stress may be induced in a patient's body by infection, trauma (e.g. wounds or burns) or surgery. Once the systemic response is activated, the physiologic and metabolic changes that follow are similar and may lead to septic shock. The metabolic response to stress involves most metabolic pathways, accelerates metabolism and leads to a negative nitrogen balance and muscle wasting.

Metabolic stress has also an impact on the lungs causing metabolic stress-induced lung injuries. For example, acute respiratory distress syndrome (ARDS) is a common, devastating clinical problem arising from metabolic stress, including pneumonia, trauma or sepsis. Because of its significant mortality and morbidity, ARDS has been in the focus of extensive experimental and clinical research.

Since there is little doubt that alterations of the surfactant system contribute to lung dysfunction and the onset of ARDS, several clinical studies examined the therapeutic safety and efficacy of a surfactant replacement therapy. Clinical experience with exogenous surfactant has proven inconsistent as a therapeutic modality for adult patients with ARDS. Therefore, surfactant therapy is not recommended for routine clinical use in adult patients and is considered as a last resort treatment.

Therefore, new approaches in the prevention and treatment metabolic stress-induced lung injuries are needed.

Surprisingly, it has been found that a composition comprising
choline and
a compound selected from the group consisting of palmitate, vitamin C and vitamin E
may be used in treating or preventing metabolic stress-induced lung injury. Particularly, the metabolic stress-induced lung injury is acute lung injury (ALI) and/or acute respiratory distress syndrome (ARDS) and/or exercise-induced pulmonary hemorrhage (EIPH).

Particularly, it has been shown that the use of such a composition comprising as active constituents 16% vitamin C, 14% palmitate, 6.6% choline chloride and 0.7% vitamin E in racehorses before and during exercise sessions increases physical capacity of the horses and prevents physical stress-induced lung injury. Thus, the physical capacity of racehorses to sustain training bouts was increased, i.e. severity as well as frequency of training sessions may be enhanced. Additionally, the severity of exercise-induced hemorrhage was reduced.

There are other metabolic stress-induced diseases closely related to EIPH. These are e.g. ALI and ARDS, which involve similar pathophysiological mechanisms. Therefore, it is concluded that the composition as defined above will be effective in these conditions as well. Particularly, EIPH, ALI and ARDS involve release of reactive oxygen species (ROS), which are important components of mammalian inflammatory response. They are released during stress-induced lung injury and form a necessary component of cellular defenses against pathogens and disease processes. However, in the lungs ROS can damage pulmonary structures directly as well as indirectly by mediating the release of inflammatory mediators leading finally to the above diseases. Further details on the mechanisms in EIPH, ALI and ARDS are given below.

The goal of any form of administration of the composition of the present invention to patients suffering from metabolic stress (e.g. infection (such as pneumonia, peritonitis, sepsis, etc), trauma, critical illness, burns, wounds, after surgery or exercise) is not only to promote recovery and to accelerate return to normal physical capacity, but also to avoid any detrimental side effects. The acute phase in these patients is characterized by rapid onset of respiratory failure and arterial hypoxemia. The pathologic findings include injury in both capillary endothelium and alveolar epithelium, resulting in an influx of a protein-rich edema fluid into the airspaces. Also, a massive accumulation and activation of poly-morphonuclear leukocytes mediates the evolution of inflammation through the release of several inflammatory mediators, such as eicosanoids, platelet-activating factor, and oxidants.

Qualitative and quantitative alterations in lung surfactant composition also contribute to respiratory failure. Surfactant phospholipids are sensitive targets for phospholipases and especially for type II secretory phospholipase A2 (PLA2), a marker of inflammation, giving rise to lyso-phospholipids. Lyso-phosphatidylcholine (lyso-PC) plays a crucial role in the evolution of metabolic stress-induced lung injuries such as ARDS because it damages the alveolar epithelium, increases capillary permeability and inactivates surfactant tensioactivity. Phospholipase A2 activity also is responsible for the release of arachidonic acid and its biologically active metabolites, such as prostaglandins and leukotrienes. Moreover, secretory phospholipase A2 could lead to the generation of platelet-activating factor, a potent phospholipid mediator in inflammatory reactions, which also is possibly involved in the pathogenesis of acute lung injury.

Furthermore, another form of metabolic stress-induced lung injury, i.e. exercise-induced pulmonary hemorrhage (EIPH), is common in livestock, particularly horses, following bouts of intense exertion; it is a particular problem in racing Thoroughbreds and Standardbreds, and occurs in up to 75% of these animals. The hemorrhage is usually detected endoscopically after racing. Because EIPH does not usually result in the death of the animal, and is not an impediment to the use of the horse after the racing career is over, there have been limited studies describing the histopathology of this disease. The most extensive investigation of the gross and histologic features of EIPH was performed 20 years ago. These investigators described the clinical features of 26 EIPH-affected horses and the pathology of 19. The gross lesions of EIPH include bilaterally symmetrical dark discoloration of the pleura of dorsocaudal lung, which is firmer than normal lung (O'Callaghan et al., Equine Vet J 1987; 19:389-393). Histologically, the primary findings were scattered bronchiolitis, hemosiderophage accumulation, and fibrosis (O'Callaghan et al., Equine Vet J 1987; 19:411-418).

In spite of the frequency of EIPH in the horse population, there is a poor understanding of the pathogenesis of the disease. Many of the factors suggested to contribute to EIPH have been proposed following examination of the histology and ultrastructure of the lungs from EIPH-affected horses; hypothesized mechanisms include capillary stress failure, pulmonary fibrosis, and antecedent small airway disease. Currently, the most accepted hypothesis for EIPH pathogenesis is exercise-induced pulmonary hypertension, resulting in alveolar capillary stress failure (West et al., J Appl Physiol 1993; 75:1097-1109). However, this hypothesis does not account for the lesions of EIPH, i.e., fibrosis and bronchial circulation proliferation. Thus, the goal of any form of intervention in racing Thoroughbreds and Standardbreds during training is to prevent/ameliorate exercise-induced lung injury such as EIPH and to promote lung function while avoiding any unwanted effects such as increased concentrations of ammonia and urea in the blood.

Lung phosphatidylcholine (PC) serves as a surfactant to maintain pulmonary compliance under normal circumstances by reducing surface tension in the alveoli during exhalation and by keeping fluid out of the lungs. PC is a phospholipid consisting fundamentally of two fatty acids and a choline molecule attached to a glycerol backbone.

Choline represents, besides palmitate, an important component of the entire PC surfactant molecule. Interestingly, a choline-rich diet has been demonstrated to improve survival in a rat model of endotoxin shock (Rivera et al., Am J Physiol 1998; 275 (Gastrointest Liver Physiol 38): G862-G867). Female Sprague-Dawley rats fed chow or chow plus choline (0.025%-0.4%) for 3 days were given lipopolysaccharide (LPS) via the tail vein. Of the chow-fed rats 83% resp. 56% survived after 2.5 or 5.0 mg/kg LPS, respectively. Choline increased survival in a dose-dependent manner, with maximal effects observed at 0.4%. This dose of choline prevented mortality completely after 2.5 or 5.0 mg/kg LPS. Further, dietary choline diminished TNF-α production in alveolar macrophages by 50%. A previous study (Grove et al., J Leuco Biol 1990; 48: 38-42) demonstrated that macrophage activation by LPS was associated with an increased rate of phosphatidylcholine hydrolysis via a phospholipase-dependent mechanism.

Accordingly—without being bound to this theory—, it is assumed that supplying excess choline in the diet enhances phosphatidylcholine synthesis under conditions of stress (trauma, infection, exercise, etc.) and, thus, reduces adverse effects in the lungs mediated by metabolic stress.

Surfactant function is closely tied to the composition of PC, i.e. the specific fatty acids bound to the glycerol. Optimal function is achieved when the fatty acid is predominantly palmitate. Under normal circumstances, about 70% of the fatty acids in lung surfactant are palmitate. Palmitate is a saturated fatty acid (16:0) and the straight structure of palmitate allows close packing of the PC molecules during exhalation, which maximizes the surfactant capacity (Wright J R, Clements J A. Am Rev Respir Dis 1987; 136: 426-444). In contrast, unsaturated fatty acids (e.g. linoleic acid, 18:2) have crooked chains due to the presence of double bonds and thus decrease the surfactant capacity of PC.

Thus, the goal of specific administration of palmitate for patients suffering from metabolic stress is not only to promote surfactant synthesis, but also to maintain a high proportion of palmitate in their lung PC and to avoid an increased incorporation of unsaturated fatty acids.

The importance of maintaining the proper composition of lung PC was shown by a study of Martini et al (FASEB J 1999; 13: A542) in pigs. Two groups of pigs were fed diets matched calorically and in general composition (20% protein, 40% carbohydrate, 40% fat) for a period of 3 weeks. In one group, the fat was palmitate (16:0), in the other linoleate (18:2). After 3 weeks the resting pulmonary function was determined. Thereafter endotoxin was infused at 80 ng/kg/min over 30 min. Ten min after termination of the endotoxin infusion, pulmonary function was assessed again followed by sacrificing the animals. Resting pulmonary dynamic compliance was lower ($p<0.05$) in the linoleic acid group ($73\pm11$ ml/cm $H_2O$) than that in the palmitate group ($111\pm13$ ml/cm $H_2O$). After endotoxin infusion, pulmonary dynamic compliance in the linoleate group ($43\pm5$ ml/cm $H_2O$) was further decreased ($p<0.05$) in comparison to that in the palmitate group ($65\pm7$ ml/cm $H_2O$). Linoleate composition in alveolar surfactant phosphatitylcholine was $11.3\%\pm1.3\%$ in the linoleate group and $3.7\%\pm0.2\%$ in the palmitate group. Thus, a diet high in linoleate results in an increase in the proportion of linoleate incorporation in lung surfactant and this is detrimental to surfactant activity. Although the lungs have sufficient capacity to function adequately under normal conditions, but when metabolic stress is encountered, induced by endotoxin, an additional impairment of lung function occurs with increased linoleate content.

In a similar study by the same group of investigators, three groups of pigs were included to receive an isocaloric diet (20% protein, 40% carbohydrate, 40% fat). In one group the fat content consisted entirely of palmitic acid. In the second group the fat came from Intralipid, which provided predominantly linoleic acid. The third group was fed fish oil (Wolfe et al., Nutrition 2002; 18: 647-653). After 3 weeks on the diets an endotoxin challenge was performed until the pulmonary arterial pressure reached a level similar found to that found in trauma victims (40 to 50 mm Hg). Pulmonary function tests were then repeated. Lung compliance was reduced in pigs fed the linoleic and fish oil groups compared with the palmitate group before and after endotoxin. Lung compliance changes in pigs fed the linoleic acid and fish oil diets were consistent with histological evidence of vascular congestion, intra-alveolar edema and alveolar septa thickening. Changes in surfactant phosphatidylcholine composition between groups were consistent with the notion that increased unsaturated fatty acids could negatively affect surfactant function.

In burn injury, another example of metabolic stress, it was found that lung compliance decreased in pigs four days following thermal injury (Martini et al., Crit Care Med 2001; 29: 1417-1422). Further, quantification of the pulmonary surfactant kinetics (Martini et al., Am J Physiol 1999; 277 (Endocrinol Metab 40): E187-E195) demonstrated that the observed fall in lung compliance in burn injury is explained by a decrease of more than 40% in the amount of phosphatidylcholine (surfactant) in the lungs (Martini et al., 2001, supra). Thus, in burned animals the total surfactant phosphatidylcholine pool size was reduced from the control value of $2.65\pm0.05$ to $1.61\pm0.08$ μmol/g wet lung ($p<0.05$), as was the proportional contribution of palmitate to lung surfactant phosphatidylcholine composition. Decreased lung compliance impairs blood gas exchange in the lungs and this problem represents the central problem in acute lung injury (ALI) and acute respiratory distress syndrome (ARDS).

As detailed above, as a consequence of stress-mediated lung injury oxidants are released. The effect could be ameliorated by administration of an antioxidant, which is a molecule capable of slowing down or preventing the oxidation of other molecules. Oxidation is a chemical reaction that transfers electrons from a compound to an oxidizing agent. Oxidation reactions can produce free radicals, which start chain reactions that damage cells. Antioxidants terminate these chain reactions by removing free radical intermediates, and inhibit other oxidation reactions by being oxidized themselves.

As oxidative stress might be an important part of many human diseases, the use of antioxidants in pharmacology is intensively studied, particularly as treatments for stroke and neurodegenerative diseases. However, it is unknown whether oxidative stress is the cause or the consequence of disease. Antioxidants are also widely used as ingredients in dietary supplements in the hope of maintaining health and preventing diseases such as cancer and coronary heart disease.

Accordingly, the inventors assumed that the combination of (i) choline and (ii) palmitate and/or one or more antioxidants such as vitamins C and E to be useful in treating or preventing metabolic stress-induced lung injury.

Accordingly, in a first aspect the present invention relates to a composition comprising
  choline and
  a compound selected from the group consisting of palmitate, vitamin C and vitamin E
for use in treating or preventing metabolic stress-induced lung injury, wherein the metabolic stress-induced lung injury is acute lung injury (ALI) and/or acute respiratory distress syndrome (ARDS) and/or exercise-induced pulmonary hemorrhage (EIPH).

Choline is an organic compound, classified as a water-soluble essential nutrient and usually grouped within the vitamin B complex. This natural amine is found in the lipids that make up cell membranes and in the neurotransmitter acetylcholine. Adequate intakes for this micronutrient of between 425 to 550 milligrams daily, for adults, have been established by the Food and Nutrition Board of the Institute of Medicine of the National Academy of Sciences. Choline is a quaternary saturated amine with the chemical formula $(CH_3)_3N^+CH_2CH_2OHX^-$, where $X^-$ is a counterion such as chloride, salicylate, hydroxide or tartrate.

Accordingly, choline according to the present invention can be in any water-soluble form and relates to the free base and $(CH_3)_3N^+CH_2CH_2OHX^-$, where $X^-$ is a counterion. Choline compounds such as choline chloride, phosphatidyl choline, choline bitartrate, choline bicarbonate, salicylate and choline free base are water soluble and commercially available. The preferred choline compounds are choline chloride, hydroxide and tartrate. More preferably choline is used as choline tartrate.

Palmitate is a term for the salts or esters of palmitic acid. Palmitic acid, $CH_3(CH_2)_{14}COOH$ or hexadecanoic acid in IUPAC nomenclature, is one of the most common saturated fatty acids found in animals and plants. As its name indicates, it is a major component of the oil from palm trees (palm oil and palm kernel oil). For use in the composition, palmitate is conveniently employed in esterified form as triglyceride or as phospholipid. Preferably, palmitate is used as palm oil.

Vitamin C or L-ascorbic acid is an essential nutrient for humans, a large number of higher primate species, a small number of other mammalian species, a few species of birds, and some fish. Ascorbate is required for a range of essential metabolic reactions in all animals and plants. It is made internally by almost all organisms, apes and humans being a notable exception. Deficiency in this vitamin causes scurvy in humans. It is also widely used as a food additive. The pharmacophore of vitamin C is the ascorbate ion. In living organisms, ascorbate is an anti-oxidant, since it protects the body against oxidative stress, and is a cofactor in several vital enzymatic reactions.

Vitamin C is purely the L-enantiomer of ascorbate; the opposite D-enantiomer has no physiological significance. When L-ascorbate, which is a strong reducing agent, carries out its reducing function, it is converted to its oxidized form, L-dehydroascorbate. L-dehydroascorbate can then be reduced back to the active L-ascorbate form in the body by enzymes and glutathione. During this process semidehydroascorbic acid radical is formed. Ascorbate free radical reacts poorly with oxygen, and thus, will not create a superoxide. Instead two semidehydroascorbate radicals will react and form one ascorbate and one dehydroascorbate. With the help of glutathione, dehydroxyascorbate is converted back to ascorbate. L-ascorbate is a weak sugar acid structurally related to glucose which naturally occurs either attached to a hydrogen ion, forming ascorbic acid, or to a metal ion, forming a mineral ascorbate.

Ascorbic acid is a reducing agent and can reduce, and thereby neutralize, reactive oxygen species such as hydrogen peroxide. In addition to its direct antioxidant effects, ascorbic acid is also a substrate for the antioxidant enzyme ascorbate peroxidase.

Vitamin E is a generic term for tocopherols and tocotrienols. Vitamin E is a family of α-, β-, γ-, and δ-tocopherols and the corresponding four tocotrienols. Vitamin E is a fat-soluble antioxidant that stops the production of reactive oxygen species formed when fat undergoes oxidation. Of these, α-tocopherol has been most studied as it has the highest bioavailability. It has been claimed that α-tocopherol is the most important lipid-soluble antioxidant, and that it protects cell membranes from oxidation by reacting with lipid radicals produced in the lipid peroxidation chain reaction. This would remove the free radical intermediates and prevent the oxidation reaction from continuing. The oxidised α-tocopheroxyl radicals produced in this process may be recycled back to the active reduced form through reduction by other antioxidants, such as ascorbate, retinol or ubiquinol. Other forms of vitamin E have their own unique properties. For example, γ-tocopherol (also written as gamma-tocopherol) is a nucleophile that can react with electrophilic mutagens.

Compared with tocopherols, tocotrienols are poorly studied. Current research directions are starting to give more prominence to the tocotrienols, the lesser known but more potent antioxidants in the vitamin E family. Tocotrienols have specialized roles in protecting neurons from damage, cancer prevention and cholesterol reduction by inhibiting the activity of HMG-CoA reductase; δ-tocotrienol blocks processing of sterol regulatory element—binding proteins (SREBPs). Oral consumption of tocotrienols is also proven to protect against stroke-associated brain damage in vivo.

The composition according to the present invention comprises (i) choline and (ii) a compound selected from the group consisting of palmitate, vitamin C and vitamin E. Accordingly, the composition may comprise
  choline and palmitate,
  choline and vitamin C,
  choline and vitamin E,
  choline, palmitate and vitamin C,
  choline, palmitate and vitamin E,
  choline, vitamin C and vitamin E, or
  choline, palmitate, vitamin C and vitamin E.

Additionally, the composition may comprise also one or more auxiliaries/excipients. These are inactive substances used as a carrier for the active ingredients of a medication.

In many cases, an "active" substance may not be easily administered and absorbed by the human body; in such cases the substance in question may be dissolved into or mixed with an excipient. Excipients are also sometimes used to bulk up formulations that contain very potent active ingredients, to allow for convenient and accurate dosage. In addition to their use in the single-dosage quantity, excipients can be used in the manufacturing process to aid in the handling of the active substance concerned. Depending on the route of administration, and form of medication, different excipients may be used. For oral administration tablets and capsules are used. Suppositories are used for rectal administration.

Often, once an active ingredient has been purified, it cannot stay in purified form for long. In many cases it will denature, fall out of solution, or stick to the sides of the container. To stabilize the active ingredient, excipients are added, ensuring that the active ingredient stays "active", and, just as importantly, stable for a sufficiently long period of time that the shelf-life of the product makes it competitive with other products.

Typical auxiliaries/excipients are—without limitation—antiadherents, binders, coatings, disintegrants, fillers, diluents, flavours, colours, glidants, lubricants, preservatives, sorbents and sweeteners. Antiadherents are used to reduce the adhesion between the powder (granules) and the punch faces and thus prevent sticking to tablet punches. Most commonly used is magnesium stearate. Binders hold the ingredients in a tablet together. Binders ensure that tablets and granules can be formed with required mechanical strength, and give volume to low active dose tablets. Binders are usually starches, sugars, cellulose or modified cellulose such as microcrystalline cellulose, hydroxypropyl cellulose, lactose, or sugar alcohols like xylitol, sorbitol or maltitol. Solution binders are dissolved in a solvent (for example water or alcohol can be used in wet granulation processes). Dry binders are added to the powder blend, either after a wet granulation step, or as part of a direct powder compression (DC) formula. Tablet coatings protect tablet ingredients from deterioration by moisture in the air and make large or unpleasant-tasting tablets easier to swallow. For most coated tablets, a hydroxy propylmethylcellulose (HPMC) film coating is used which is free of sugar and potential allergens. Occasionally, other coating materials are used, for example synthetic polymers, shellac, corn protein (e.g. zein) or polysaccharides such as ethylcellulose or carboxy methylethyl cellulose. Capsules are coated with gelatin. Disintegrants expand and dissolve when wet causing the tablet to break apart in the digestive tract, releasing the active ingredients for absorption. Fillers fill out the size of a tablet or capsule, making it practical to produce and convenient for the consumer to use. By increasing the bulk volume, the fillers make it possible for the final product to have the proper volume for patient handling. Examples of fillers include: cellulose, calcium phosphate, vegetable fats and oils, lactose, sucrose, glucose, mannitol, sorbitol, calcium carbonate, and magnesium stearate. Flavours can be used to mask unpleasant tasting active ingredients and improve the likelihood that the patient will complete a course of medication. Flavourings may be natural (e.g. fruit extract) or artificial. Colours are added to improve the appearance of a formulation. Colour consistency is important as it allows easy identification of a medication. Glidants are used to promote powder flow by reducing interparticle friction and cohesion. These are used in combination with lubricants as they have no ability to reduce die wall friction. Examples include colloidal silicon dioxide, talc and $MgCO_3$. Lubricants prevent ingredients from clumping together and from sticking to the tablet punches or capsule filling machine. Lubricants also ensure that tablet formation and ejection can occur with low friction between the solid and the wall. Common minerals like talc or silica, and fats, e.g. vegetable stearin, magnesium stearate or stearic acid are the most frequently used lubricants in tablets or hard gelatin capsules. Sorbents are used for tablet/capsule moisture-proofing by limited fluid sorbing (taking up of a liquid or a gas either by adsorption or by absorption) in a dry state. Sweeteners are added to make the ingredients more palatable, especially in chewable tablets such as antacid or liquids like cough syrup. Therefore, tooth decay is sometimes associated with cough syrup abuse. Sugar can be used to disguise unpleasant tastes or smells.

The feature "a composition" is intended to relate to "one or more compositions". Accordingly, the active compounds of (i) and (ii) of the composition(s) may be administered simultaneously or consecutively, optionally also at different times.

The composition of the present invention is used in treating or preventing metabolic stress-induced lung injury, particularly wherein the metabolic stress-induced lung injury is acute lung injury (ALI) and/or acute respiratory distress syndrome (ARDS) and/or exercise-induced pulmonary hemorrhage (EIPH).

In one example, metabolic stress-induced lung injury is a complication that frequently occurs in critically ill patients and is known under the term of "Acute Lung Injury (ALI) or "Acute Respiratory Distress Syndrome" (ARDS), the more severe form of ALI. ALI and ARDS are responsible for significant morbidity and mortality in critically ill patients. Regardless of the underlying illness, the clinical and pathologic manifestations of ALI/ARDS are very similar, indicating the existence of final common pathways that represent potential therapeutic targets. In essence, these syndromes reflect severe injury leading to dysfunction and compromise of the barrier properties of the pulmonary endothelium and epithelium as a consequence of an unregulated acute inflammatory response. In this hypothetical construct, an initiating event (e.g. wound, burn, surgery, infection, sepsis, hemorrhagic shock, trauma, multiple transfusions, pancreatitis, etc.) leads to activation of the acute inflammatory response on a systemic level. One of the earliest manifestations is activation of pulmonary endothelium and macrophages (alveolar and interstitial), upregulation of adhesion molecules, and production of cytokines and chemokines that induce a massive sequestration of neutrophils within the pulmonary microvasculature. These cells transmigrate across the endothelium and epithelium into the alveolar space and release a variety of cytotoxic and proinflammatory compounds, including proteolytic enzymes, reactive oxygen species (ROS) and nitrogen species, cationic proteins, lipid mediators, and additional inflammatory cytokines. This perpetuates a vicious cycle by recruiting additional inflammatory cells that in turn produce more cytotoxic mediators, ultimately leading to profound injury to the alveolo-capillary membrane and respiratory failure. It is noteworthy that although the most obvious initial manifestations may be respiratory in nature, ALI/ARDS are part of a systemic process involving microvascular dysfunction of diverse organs including the heart, kidneys, gut, liver, muscle, and brain manifest as multi-organ dysfunction.

Acute lung injury (ALI) is a diffuse heterogeneous lung injury characterized by hypoxemia, non cardiogenic pulmonary edema, low lung compliance and widespread capillary leakage. ALI is caused by any stimulus of local or systemic inflammation, principally sepsis. As detailed above ARDS is the more severe form of ALI.

ALI and ARDS may be defined as:
Bilateral pulmonary infiltrates on chest x-ray
Pulmonary Capillary Wedge Pressure<18 mm Hg (2.4 kPa)
PaO2/FiO2*<300=ALI
PaO2/FiO2<200=ARDS Primary ALI is caused by a direct injury to the lung (e.g. pneumonia). Secondary ALI is caused by an indirect insult (e.g. pancreatitis, peritonitis, sepsis, etc). There are two stages—the acute phase characterized by disruption of the alveolar-capillary interface, leakage of protein rich fluid into the interstitium and alveolar space and extensive release of cytokines and migration of neutrophils. A later reparative phase is characterized by fibroproliferation, and organization of lung tissue. The patient has low lung volumes, atelectasis, loss of compliance, ventilation-perfusion mismatch (increased deadspace) and right to left shunt.

Clinical features are—severe dyspnea, tachypnea and resistant hypoxemia.

The diagnosis of ALI/ARDS is based on a definition that includes bilateral pulmonary infiltrates on chest radiographs, impaired oxygenation, and the absence of clinical evidence of elevated left atrial pressure. ALI/ARDS is the clinical result of a group of diverse processes, which range from physical or chemical injury, to extensive activation of innate inflammatory response. All these processes damage the integrity of the alveolar-capillary barrier causing increased alveolar-capillary permeability and an influx of protein-rich fluid into the alveolar space. This alveolar flooding results in hypoxemia, inactivated surfactant, intrapulmonary shunt, and impaired alveolar ventilation. At present the treatment of ARDS is largely supportive in nature, keeping patients alive while allowing their lungs to heal, and minimizing further pulmonary insult.

Another example of metabolic stress-induced lung injury is exercise-induced lung injury. Exercise relates to any kind of intense physical activity or active performance and may involve physical stress. Exercise-induced lung injury may be for example "Exercise-Induced Pulmonary Hemorrhage" (EIPH) in e.g. horses, dogs and pigs following intense activity or exercise. EIPH is a particular problem in racing Thoroughbreds and Standardbreds, and occurs in up to 75% of these animals. The hemorrhage is usually detected endoscopically after racing, originates from the pulmonary vasculature and is distributed predominantly bilaterally in the dorsocaudal lung lobes. In severe cases it may manifest itself as blood discharging from a horse's nostrils (epistaxis). The affliction occurs when blood enters the air passages of a horse's lung, due to fractured lung capillaries. If a horse does not exhibit epistaxis but is suspected to have EIPH, an endoscopic exam is performed soon after the horse is exercised. It is believed that nearly all horses experience EIPH, when exposed to strenuous exercise, and it has the potential to decrease lung function over time. As already mentioned above, reactive oxygen species (ROS) are an important component of the mammalian inflammatory response. They are released during tissue injury and form a necessary component of cellular defences against pathogens and disease processes. The effects of ROS are normally limited or neutralized by a multifactorial system of antioxidant defences, although excessive production and/or deficient antioxidant defences may expose healthy tissue to oxidant damage. In the lung, ROS can damage pulmonary structures both directly and by initiating the release of other inflammatory mediators, including proteases and eicosanoids. Vascular endothelial cells are particularly susceptible to ROS-induced oxidant injury in the lung, and both the destruction of the pulmonary blood-gas barrier and the action of vasoactive substances will increase pulmonary vascular resistance. Moreover, ROS can degrade endothelium-derived nitric oxide (NO), a major pulmonary vasodilator, thereby, with exercise, synergistically increasing the likelihood of stress failure of pulmonary capillaries, a contributing factor to EIPH.

The diagnosis of EIPH is based on the detection of lung hemorrhage by endoscopy after exercising or racing, but in severe cases it manifests itself by epistaxis, i.e. bloody discharge from the horse's nostrils.

A prevention or preventive measure is a way to avoid a disease or disorder in the first place, and generally it will not help someone who is already ill (though there are exceptions). For instance, many babies in developed countries are given a polio vaccination soon after they are born, which prevents them from contracting polio. But the vaccination does not work on patients who already have polio. A treatment or cure is applied after a medical problem has already started.

A treatment treats a problem, and may lead to its cure, but treatments more often ameliorate a problem only for as long as the treatment is continued. For example, there is no cure for AIDS, but treatments are available to slow down the harm done by HIV and delay the fatality of the disease. Treatments don't always work. For example, chemotherapy is a treatment for some types of some cancers, which may in some cases enact a cure, but not in all cases for all cancers.

The composition may be administered to the patient by any suitable route, including orally (enterally) or intravenously (parenterally). The composition may be conveniently administered in form of an aqueous solution, i.e a suspension. The composition in a form suitable for enteral or parenteral application is preferably in aqueous or powder form, whereby an aqueous solution, water or buffer is conveniently added to the powder prior to use. It will be appreciated that, for acute treatment, the parenteral application route may be preferred.

In a preferred embodiment the composition comprises choline and palmitate, and optionally also vitamin C and/or E. Accordingly, the composition may comprise
choline and palmitate,
choline, palmitate and vitamin C,
choline, palmitate and vitamin E, or
choline, palmitate, vitamin C and vitamin E.

Typical daily doses ("effective" amounts) of the compounds—as far as present—may be as follows:
choline may preferably be present in amount of from 1 to 30 mg/kg body weight (BW), preferably 3 to 25 mg/kg BW, even more preferred 5 to 15 mg/kg BW of free base,
palmitate is present in amount of from 40 to 2000 mg/kg BW, preferably 100 to 1500 mg/kg BW, even more preferred 200 to 1000 mg/kg BW,
vitamin C may preferably be present in amount of from 1 to 100 mg/kg BW, preferably 5 to 50 mg/kg BW, even more preferred 10 to 35 mg/kg BW, and/or
vitamin E may preferably be present in amount of from 0.05 to 10 mg/kg BW, preferably 0.1 to 5 mg/kg BW, even more preferred 0.2 to 2 mg/kg BW.

The amounts of the above compounds to be administered depend largely on the patient's specific requirements and may vary depending on the patient's condition, sex, weight, disease to be treated or prevented etc. Such daily amounts are suitable for treatment of the desired effect as well as for prophylaxis.

In a preferred embodiment, metabolic stress-induced lung injury is trauma-induced lung injury or exercise-induced lung injury, especially wherein exercise is associated with increased breathing activity.

A trauma is any body wound or shock including hemorrhagic shock due to extensive blood loss produced by sudden physical injury, as from accident, burn injury, or impact. Trauma patients normally require specialized care, including surgery, mechanical ventilation, blood transfusion, etc., better known under the term "emergency medicine".

In accordance with the present invention the active compounds defined herein in the context of the present invention (choline, palmitate, vitamin C and/or E) are the only pharmaceutically active compounds for use in treating or preventing trauma-induced lung injury.

Besides the medical use of the composition of the present invention (see above), it is also contemplated to eat or feed the composition as specified above for non-medical uses, e.g. for non-medical increase of physical capacity. A non-medical use may be the use as a supplement, also known as food supplement or feed supplement or nutritional supplement or dietary supplement, which is a preparation intended to provide nutrients, such as vitamins, minerals, fiber, fatty acids or amino acids, that are missing or are not consumed in sufficient quantity in a subject's diet. Many countries define dietary supplements as foods. In accordance with the legal regulations it is noted that a dietary supplement would be considered to be an unauthorized new drug and in violation of the applicable regulations and statutes, if it claims to cure, mitigate, or treat a disease. Accordingly, it is evident that a method relating to increasing physical capacity of mammalian livestock by use of a (food, feed, nutritional or dietary) supplement is not a therapeutic method.

Surprisingly, it has now been found that support of racehorses (Thoroughbreds and Standardbreds) during training is able to increase their physical capacity. The support was given by feeding a supplement comprising substantial amounts of palmitate and choline and, optionally, selected other components such as selected vitamins. It has been shown that the physical capacity of racehorses fed with a composition comprising as active constituents 16% vitamin C, 14% palmitate, 6.6% choline chloride and 0.7% vitamin E was increased, i.e. they were able to sustain training bouts and severity as well as frequency of training sessions could be enhanced.

Accordingly, in another aspect, the present invention relates to a method for increasing physical capacity of mammalian livestock comprising feeding to the mammalian livestock
  a supplement comprising
  choline and
  a compound selected from the group consisting of palmitate, vitamin C and vitamin E.

The human or animal body can make some choline, but it is generally recognized that it is important to get dietary choline as well. Although most foods have at least a little choline, some subjects may have to pay close attention to get enough in their diets, particularly if they do not eat many whole eggs and if they likely subject to physical stress, particularly repeated exercise.

The most often available choline supplement is lecithin, derived from soy or egg yolks, often used as a food additive. Phosphatidylcholine is also available as a supplement, in pill or powder form. Supplementary choline is also available as choline chloride, which comes as a liquid due to its hydrophilic properties. Choline chloride is sometimes preferred as a supplement because phosphatidylcholine can have gastrointestinal side effects.

It is noted that choline, palmitate, vitamin C and vitamin E are as defined above in the context of the composition of the present invention, including the above preferred embodiments, as far as applicable to non-medical use.

The term "livestock" refers to any breed or population of animal kept by humans for a useful, commercial purpose. This can mean domestic animals, semi-domestic animals, or captive wild animals. Semi-domesticated refers to animals which are only lightly domesticated or of disputed status. These populations may also be in the process of domestication. The term "mammalian livestock" refers to livestock of the class mammalia.

The term "physical capacity" relates to a subject's capacity to perform physical activity. In creased capacity may relate to increased velocity, the ability to perform an action for an increased period, the ability to perform the same action within a shorter time, or the ability to perform, repeatedly, the same action for the same time but with an increased intensity.

Feeding is the process by which animals obtain food. The supplement can be fed to the animal livestock simultaneously with the normal fodder or at a different time. The supplement may be mixed with the fodder are it may be given to the animal in a separate form.

In a preferred embodiment the supplement comprises choline and palmitate, and optionally also vitamin C and/or E. Further details on suitable combinations and typical daily doses of the compounds are given above.

Preferably, the mammalian livestock is selected from the group consisting of horse, camel, dog, cattle, and donkey, preferably horse, especially a racehorse.

In a preferred embodiment, the mammalian livestock is an animal used in animal racing. Typical animals used for animal races are—without limitation—horses (preferably Thoroughbreds and Standardbreds), dogs (e.g. greyhounds) and camels.

In a preferred embodiment increased physical capacity is increased intensity of physical capacity; increased duration of physical capacity, particularly duration of active performance; or reduced duration of recovery.

The feature "increased intensity of physical capacity" relates to a situation in which the subject is capable of performing a physical activity for the same period of time, but with a higher intensity. For an animal used in racing this could be, for example, racing with the same speed for the same period, but with a higher load or a higher incline.

The feature "increased duration of physical capacity" relates to a situation in which the subject is capable of performing the same physical activity (same intensity) for a longer period of time. For an animal used in racing this could be, for example, racing with the same speed for a longer period.

The feature "reduced duration of recovery" relates to a situation in which the time needed by subject for recovery between two phases of activity is reduced. For an animal trained for contests, competitions or racing this could be, for example, that the recovery time between training lessons, units or contests could be reduced.

Suitable methods for determining physical capacity, intensity of physical capacity, duration of physical capacity, particularly duration and frequency of phases with physical activity and duration of recovery are well known to the skilled person.

By "increase in physical capacity" is meant any significant augment of physical capacity as defined above. Accordingly, by "reduced duration of recovery" is meant any significant decrease of the time needed by subject for recovery between phases of activity, i.e. repeated exercise. Methods of determining significant differences between to values are well known to the skilled person and include, for example, Student's t-test and Chi square test. In the context of the present invention, the capability of a subject after administration of the supplement for a sufficient time is compared to the capability of a control subject, in general a subject not having obtained the supplement.

EXAMPLES

Example 1

A composition comprising as active constituents per 150 g dose 16% vitamin C, 14% palmitate, 6.6% choline chloride, 2% green tea extract and 0.7% vitamin E was given orally in powder form daily over a period of 7 days before the race. It was administered to a four year old Arabian stallion. The stallion had suffered from cases of acute EIPH following exercise bouts, which were unsuccessfully treated resulting in unfitness to compete. Blood and urine samples taken before and after one week of receiving the supplement showed a significant improvement in the stallion's health and the frequency/severity of EIPH was reduced at the same time. The stallion's ability to exercise and race (competitively) continued to improve during four months of treatment with the supplement.

Example 2

The composition of Example 1 was administered to a five year old American Thoroughbred that was suffering from exercise-induced EIPH during regular training sometimes resulting in epistaxis. Furthermore, the horse was several times taken out of racing following at least 1 episode of epistaxis during racing. After regular consumption of the supplement for four weeks the horse's capacity to exercise and race improved considerably and no cases of epistaxis were observed.

REFERENCES

Wright J R, Clements J A. Metabolism and turnover of lung surfactant. Am Rev Respir Dis 1987; 136: 426-444

Martini W Z, Irtun O, Barrow R E, Wolfe R R. Dietary effects of surfactant composition and pulmonary function. FASEB J 1999; 13: A542 (abstract)

Wolfe R R, Martini W Z, Irtun O, Hawkins H K, Barrow R E. Dietary fat composition alters pulmonary function in pigs. Nutrition 2002; 18: 647-653

Martini W Z, Irtun O, Chinkes D L, Barrow R E, Wolfe R R. Surfactant phosphatidylcholine in thermally injured pigs. Crit Care Med 2001; 29: 1417-1422

Martini W, Chinkes D L, Barrow R E, Wolfe R R. Lung surfactant kinetics in conscious pigs. Am J Physiol 1999; 277 (Endocrinol Metab 40): E187-E195

Rivera C A, Wheeler M D, Enemoto N, Thurman R G. A choline-rich diet improves survival in a rat model of endotoxin shock. Am J Physiol 1998; 275 (Gastrointest Liver Physiol 38): G862-G867

Grove R I, Allegretto N J, Kiener P A, Warr G A. Lipopolysaccharide (LPS) alters phosphatidylcholine metabolism in elicited peritoneal macrophages. J Leuco Biol 1990; 48: 38-42

O'Callaghan M W, Pascoe J R, Tyler W S, Mason D K: Exercise-induced pulmonary haemorrhage in the horse: results of a detailed clinical, post mortem and imaging study. II. Gross lung pathology. Equine Vet J 1987; 19:389-393

O'Callaghan M W, Pascoe J R, Tyler W S, Mason D K: Exercise-induced pulmonary haemorrhage in the horse: results of a detailed clinical, post mortem and imaging study. V. Microscopic observations. Equine Vet J 1987; 19:411-418

West J B, Mathieu-Costello O, Jones J H, Birks E K, Logemann R B, Pascoe J R, Tyler W S: Stress failure of pulmonary capillaries in racehorses with exercise induced pulmonary hemorrhage. J Appl Physiol 1993; 75:1097-1109

The invention claimed is:

1. A method of treating exercise-induced pulmonary hemorrhage (EIPH), comprising administering to a subject selected from a horse or dog in need thereof a composition comprising choline present in an amount of 1 to 30 mg/kg body weight (BW) of free base, palmitate present in an amount of from 40 to 2000 mg/kg BW, vitamin C present in an amount from 1 to 100 mg/kg BW and vitamin E present in an amount of from 0.05 to 10 mg/kg BW; wherein the composition is administered orally or intravenously.

2. The method of claim 1, wherein choline, palmitate, vitamin C and vitamin E are the only pharmaceutically active compounds used in treating EIPH.

3. The method of claim 1, wherein the subject is a horse.

4. The method of claim 3, wherein the horse is used in animal racing.

5. The method of claim 3, wherein the horse is a racehorse.

* * * * *